United States Patent [19]

Fink et al.

[11] Patent Number: 5,370,692

[45] Date of Patent: Dec. 6, 1994

[54] RAPID, CUSTOMIZED BONE PROSTHESIS

[75] Inventors: David J. Fink, Marble Cliff; Salvatore T. DiNovo; Thomas J. Ward, both of Columbus, all of Ohio

[73] Assignee: Guild Associates, Inc., Hilliard, Ohio

[21] Appl. No.: 929,449

[22] Filed: Aug. 14, 1992

[51] Int. Cl.$^5$ .............................................. A61F 2/28
[52] U.S. Cl. ..................................... 623/16; 623/66
[58] Field of Search ............................. 623/16, 18, 66

[56] References Cited

U.S. PATENT DOCUMENTS 4,936,862 4/1988 Walker et al. ....................... 623/18

OTHER PUBLICATIONS

C. J. Damien and J. R. Parsons, "Bone Graft and Bone Graft Substitutes: A Review of Current Technology and Applications", *J. Appl. Biomater.*, vol. 2, 1991, pp. 187–208.
R. Z. LeGeros, "Calcium Phosphate Materials in Restorative Dentistry: A Review", *Adv Dent Res*, vol. 2, No. 1, Aug. 1988, pp. 164–180.
R. Z. LeGeros et al., "Significance of the Porosity and Physical Chemistry of Calcium Phosphate Ceramics Biodegradation-Bioresorption", Annals New York Academy of Sciences, vol. 523, 1988, pp. 268–271.
K. DeGroot et al., "Significance of the Porosity and Physical Chemistry of Calcium Phosphate Ceramics Dental and Other Head and Neck Uses", Annals New York Academy of Sciences, vol. 523, 1988, pp. 272–275.
J. E. Lemons et al., "Significance of the Porosity and Physical Chemistry of Calcium Phosphate Ceramics Orthopedic Uses", Annals New York Academy of Sciences, vol. 523, 1988, pp. 278–282.
K. DeGroot, "Effect of Porosity and Physiochemical Properties on the Stability, Resorption, and Strength of Calcium Phosphate Ceramics", Annals New York Academy of Sciences, vol. 523, 1988, pp. 227–233.
E. N. Kaplan, "3-D CT Images for Facial Implant Design and Maufacture", *Clin. Plast. Surg.*, vol. 14, No. 4, 1987, pp. 663–676.
M. J. Cima et al., "Three Dimensional Printing: Form, Materials, and Performance", Quarterly Report 1991, Proceedings of the Solid Free-form Fabrication Symposium, University of Texas, 1991, pp. 187–194.
U. Lakshminarayan et al., "Selective Laser Sintering of Ceramic Materials", Proceedings of the Solid Freeform Fabrication Symposium, University of Texas, 1990, pp. 16–26.
J. W. Barlow et al. "Analysis of Selective Laser Sintering", 1991, pp. 1–5.
E. Sachs et al., "Three Dimensional Printing: Ceramic Shells and Cores for Casting and Other Applications", Proceedings of the Second International Conference on Rapid Prototyping, University of Dayton, 1991 pp. 39–53.
U. Lakshminarayan et al., "Microstructural and Mechanical Properties of $AL_2O_3/P_2O_5$ and $Al_2O_3/B_2O_3$ Composites Fabricated by Selective Laser Sintering", Proceedings of the Solid Freeform Fabrication Symposium, University of Texas, 1991, pp. 205–212.
"Somatom HiQ-S: Perfecting the Art of CT", Seimens Medical Systems, Inc., 1990 sales literature.
B. K. Milthorpe, "Three Dimensional Reconstruction of Biomaterial Histrological Images", Proceedings of (List continued on next page.)

*Primary Examiner*—Randy C. Shay
*Attorney, Agent, or Firm*—Frank H. Foster

[57] ABSTRACT

Prosthetic bone implants are fabricated to approximately replicate a patient's original bone. Medical computer aided imaging techniques are applied to generate a data base representing the size and shape of the original bone in a three dimensional coordinate system. The implantable replica is fabricated using the data base and free form manufacturing to sequentially solidify adjoining, cross-sectional intervals of a fluid material. Appropriate fluid materials include ceramic particles which may be selectively bonded by sintering or bonding with a polymer, and a monomer which is polymerized at selected regions by an incident laser beam.

13 Claims, 2 Drawing Sheets

OTHER PUBLICATIONS the Fourth World Biomaterials Congress, Berlin, Federal Republic of Germany, Apr. 1992, p. 564.

M. Erbe et al., "Geometrically Surface Structured Stereolithography Acrylic Resin and Titanium Implants", Proceedings of the Fourth World Biomaterials Congress, Berlin, Federal Republic of Germany, Apr. 1992, p. 165.

S. J. Bresina, "The Treatment of Bone Defects", Proceedings of the Fourth World Biomaterials Congress, Berlin, Federal Republic of Germany, Apr. 1992, p. 207.

T. Truby, "Growing a Human Skull", *Med. Equip. Designer*, Jul. 1992, pp. M8–10.

M. Burns, "Introduction to Desktop Manufacturing and Rapid Prototyping", Rapid Prototyping: System Selection and Implementation Guide, 1992, pp. 2–6.

T. Ward et al., "The Evaluation of Component Prototyping and Reverse Engineering Systems", Final Report to U.S. Army Chemical Research, Development and Engineering Center, Nov. 1990, pp. 1–39.

5,370,692

RAPID, CUSTOMIZED BONE PROSTHESIS

TECHNICAL FIELD

This invention relates to the fabrication of prosthetic implants to replace bone and more particularly relates to the use of computer based imaging and manufacturing techniques to replicate the hard tissue being replaced by the prosthesis.

BACKGROUND ART

Wounds of war have always horrified civilian populations. Indeed, for all human history, the recognition of attendant physical mutilation has probably been the single most effective limitation on the frequency and scale of conflicts. It is only within the past century that even crude forms of reconstructive surgery were practical. However, the parallel revolutions in computer science and human-focused biotechnology now open an unprecedented opportunity to modern military medicine: to make a wounded soldier whole and functional to a degree that rivals mythology.

CERAMIC IMPLANTS

It has been only slightly more than two decades since the discovery by Hench and his co-workers that a direct chemical bond can form between certain "bioactive" glass-ceramic materials and bone, thereby potentially stabilizing dental or orthopaedic implants made from these materials. In the meantime, the investigation of other chemical formulations (including many ceramics and composites), physical forms (e.g., dense or porous particulates and solids, coatings, and composites), and clinical applications have progressed rapidly.

Most research into the use of bioactive materials is now focused on either:

1. glasses or glass-ceramic, primarily compositions from the $SiO_2$—$P_2O_5$—$CaO$—$Na_2O$ system, or
2. calcium phosphate compositions, primarily $\beta$-tricalcium phosphates ($\beta$-TCP), $Ca_3(PO_4)_2$ and calcium hydroxylapatite (HA), $Ca_{10}(PO_4)_6(OH)_2$, and combinations of the two.

Generally, the calcium phosphate ceramics may be somewhat easier to produce and/or obtain commercially, and are receiving an increasing share of the research and clinical attention. $\beta$-TCP is normally observed to biodegrade much more rapidly than HA, which until recently was believed to be non-resorbable. Such bioactive ceramics are generally considered to be osteoconductive (i.e., providing an appropriate scaffold that permits ingrowth of vasculature and osteoprogenitor cells), as opposed to osteoinductive, which implies a more active process in which the matrix recruits osteoprogenitor cells from the local tissue or circulation.

Current or potential applications for these materials include:

DENTAL AND OTHER HEAD AND NECK USES

Craniofacial Applications
Augmentation—Ridge; Mandibular; Zygomatic; Chin
Reconstruction—Periodontal; Mandibular; Orthognathy; Bone Grafting; Cranioplasty; Orbital floor; Anterior nasal spine
Prosthetic Implants
Subperiosteal
Endosteal—Endosseous implants; Endodontic pins: Orthodontic pins
Transosseous—Transmandibular
Otological Applications
Ossicular reconstruction
Canal wall prostheses

ORTHOPEDIC USES

Bone Graft Substitutes
Augmentation—Delayed or failed unions; Arthrodesis (fusion of joint); Bone graft donor sites; Mechanically stable cystic defects; Revision or primary joint replacement
Replacement—Vertebral body defects; Segmental bone defects;
Mechanically unstable subchondral defects (e.g., tibial plateau fractures and large traumatic defects; Grafting around prostheses used for mechanical fixation
Fracture Fixation Materials
Fracture fixation devices such as plates, screws and rods;
Endoprosthese such as joint replacements
Coating for Fixation
Fixation of implant to bone in joint replacement;
Coated internal fixation devices
Drug Delivery Implants
Local adjuvant chemotherapy; Local antibiotic therapy;
Local delivery of bone growth factors or osteoinductive factors HA, the predominant ceramic in bone, and the composition of the bond between bioactive ceramics and bone, has been assessed to provide the following advantages in dental implantations: 1. biocompatibility; 2. absence of antigenic response; 3. availability; 4. ability to use local anesthesia during implantation; 5. low risk of infection; 6. low risk of permanent hyperesthesia; 7. lack of significant resorption; 8. high rate of good results; and 9. no need for perfect oral hygiene on the part of the patient. Most of these advantages cart be anticipated in orthopedic applications as well, although the need for a more rapid rate of resorption has been the incentive for investigation of mixtures of HA and $\beta$-TCP to produce a range of rates.

For use in these applications, calcium phosphate materials are currently produced in a variety of formats, normally by sintering particulate solids:

Particulates—range of particle sizes; variable porosity.
Moldable Forms—pastes; self-setting slurries or preformed shapes.
Block Forms—designed geometries such as rods, cones, spheres, and discs; variable micro- and macroporosity.
Coatings—applied to a preformed substrate by techniques such as plasma spraying, flame spraying, electrophoresis, ion beam—radio frequency sputtering, dip coating, and frit-slurry enameling.

Particulate formats were among the first bioactive ceramics taken to the clinic, but these materials have the disadvantages 1) they cannot be used where implant strength is required and 2) particle migration often occurs in the implant site, decreasing the effectiveness of the material. To minimize the latter problem, many attempts have been made to use biodegradable materials to agglomerate and mold the particles during implantation.

In clinical applications in which strength of the ceramic implant is a significant factor (e.g., craniofacial augmentation or reconstruction; bone replacement; fracture fixation), block forms of the material are required and shaping of the implant becomes more difficult.

Perhaps the most important physical properties of bioactive ceramics are the volume and size of the pores within the material, which strongly influences both the tensile and compressive strengths of the material and the rate of resorption and cellular colonization. Generally, pores at least 200–300 micrometers in diameter (referred to as macroporosity) are believed to be necessary in osteoconductive materials to permit ingrowth of vasculature and osteogenic cells. Microporous ceramics, on the other hand, with pores only a few micrometers in diameter, do not permit cellular invasion, and in most cases, are likely to be more difficult to stabilize in the implant site. An example of an implant material selected for its consistent macroporosity is the "replamineform" calcium phosphate structures derived by chemically transforming a variety of corals (initially calcium carbonate), which are composed of a network of interconnecting pores in the range of approximately 200 $\mu$m diameter. HA materials of this type are marketed by Interpore Orthopedics, Inc. of Irvine, Calif.

An alternative approach to the fabrication of customized ceramic implants, involving a CT-integrated computerized milling operation to produce molds or implants, has been clinically tested for facial reconstruction. Advantages of this prefabricated implant approach were identified as:

1. Contour (of facial implants) is to the underlying bone base (as opposed to the surface of the skin by standard facial moulage techniques);
2. Formamina are localized (implants are designed to avoid nerve foramina);
3. Covered areas are "visible" (no interference in the design from hair or dressings);
4. Soft-tissue contours can be evaluated;
5. Pre-existing implants can be evaluated;
6. Volume measurements can be obtained;
7. Local anatomy can be better visualized;
8. Models are provided for "practice surgery";
9. Templates can be designed for bone graft surgery;
10. An archive can be maintained for clinical re-evaluation and academic study;
11. Prefabricated grafts minimize the time for implant sculpting in surgery, while the patient is anesthetized, and generally are much more accurate reconstructions of the desired bone than can be accomplished by hand;
12. There is no need for a second surgical site, as in autogenous graft surgery.

In the CT-integrated milling operation described, implants can be made directly by milling the solid ceramic, or by preparing a "negative" mold of the implant, then molding the implant using a formable ceramic composition. Direct milling is difficult with macroporous bioceramics, including the coralline HA materials. A moldable HA-collagen composite material has, therefore, been clinically tested with good results in low-strength indications. However, the composite is relatively friable, loses strength when moistened, and is not suitable where structural strength is required, for example, for long bone or mandibular reconstructions. In addition, control of implant macroporosity is a significant constraint when using the composite molding technique.

FREE-FORMING MANUFACTURING

The terms free-forming manufacturing (FFM), desktop manufacturing, rapid prototyping, and several others, all describe the new manufacturing processes that enable the physical fabrication of three-dimensional computer models with a minimum of human interaction. All of the systems that are on the market or in development are based upon mathematically "slicing" a three dimensional Computer Aided Design (CAD) model and then sequentially reconstructing the cross sections (slices) of the model on top of one another using the manufacturing system's solid medium. One supplier of FFM systems, 3-D Systems (Valencia, Calif.), markets a "stereolithography" system based upon laser-mediated polymerization of photo-sensitive liquid monomer. Of the FFM processes, only two are able to work with ceramics: the "Selective Laser Sintering" system marketed by DTM Corporation (Austin, Tex.) and the "3 Dimensional Printing" system under development at the Massachusetts Institute Technology (Cambridge, Mass.). Both processes can accept the industry standard STL file format, and both research organizations are working with industry to commercialize the respective processes.

The DTM process is based upon localized sintering of ceramic powder material by a scanning laser beam. When the laser beam impinges on the surface powder, it melts, and localized bonding between particles take place. By selectively sintering sequential layers, the shape is built in a matter of hours. The build rate depends on the complexity and size of the part, power output of the laser, the coupling between the laser and the material and the rheological properties of the material. Although DTM markets only polymer-based manufacturing at this time, it is currently in the research phase of developing ceramic capabilities. To date, fabrication of ceramics, including alumina/phosphate composites, have been demonstrated in the DTM process.

The MIT process, which has not been commercialized yet, is based upon selective binding of a powder, using ink-jet techniques to distribute the binding agent, as illustrated schematically in FIG. 1. Typical devices are built from alumina powder bonded with colloidal silica, to reproduce a typical ceramic shell.

CT IMAGING

In 1979 Houndsfield and Cormack were awarded the Nobel Prize in Medicine for their contributions to Computed Tomography (CT). Since then virtually every major hospital in the world has acquired the ability to perform CT. As opposed to classical x-ray imagining, where a shadow image of a patient volume is created, CT is a two step process where 1) the patient is imaged at multiple angles through the rotation of an x-ray source, and 2) the image is manipulated in the computer to create a series of sliced images of the patient. Through the use of sophisticated computer algorithms, the sliced information can be reconstructed to form three dimensional images of the patient's tissue.

A complexity of the manipulation process to create the FFM design file is the isolation of the specific tissue of interest from the surrounding tissue, a process (often relatively subjective) termed "segmentation". This selection process can be based upon matching grey-scale intensities directly from the CT file without operator interaction.

In the CT process each volume pixel (voxel) in a patient cross section is assigned a CT number (in Houndsfield units) based upon the physical density of the material with respect to water. These numbers are stored in 256×256 or 512×512 square array format. This information is manipulated in the computer to show corresponding grey or color scales for selected tissue on the computer display. This array-formatted information can also be transferred from the CT scanner into graphic engineering computers for subsequent data manipulation as demonstrated, for example, by Kaplan in the development of the integrated ceramic milling system.

Preliminary investigations, at the Medical College of Ohio, for example, have also demonstrated that relatively crude FFM models of complex anatomical structures can be prepared from MRI image files by the stereolithography system from 3-D Systems.

BRIEF DISCLOSURE OF INVENTION

The invention involves a therapeutic approach that will create customized prosthetic devices for hard tissue reconstruction. Rapid manufacturing technology can produce implants that reproduce original tissue size and shape while simultaneously maximizing the rate and quality of cell-mediated hard tissue healing. This requires integration of several independently developing technologies designed to: provide physical characteristics of the patient's original hard tissue; permit customized manufacturing by modern techniques; and optimize the rate of healing by incorporating the patient's own bone-producing cells into the implant.

Imaging technology is used first to define hard tissue characteristics (size, shape, porosity, etc.) before the trauma occurs ("pre-trauma" file) by archival use of available imaging techniques (CT, MRI, etc.). The loss of hard tissue is determined by imaging in the locale of the affected tissue after the injury ("post-trauma" file). Then the physical properties of the customized prosthetic device is specified by comparison of the pre-trauma and post-trauma files to produce a solid model "design" file. This specification may also involve secondary manipulation of the files to assist in surgical implantation and to compensate for anticipated healing process. The design file is mathematically processed to produce a "sliced file" that is then used to direct a "rapid manufacturing" system to construct a precise replica of the design file in a resorbable ceramic material to produce the implant. The unique porosity characteristics (potentially adaptable to specific patients) of the missing hard tissue structures may then be reproduced. Autologous cells, derived from the patient's post-trauma tissue, are cultured and then used to "seed" the cells onto the ceramic matrix under conditions appropriate to maximize cell attachment and function. The implanted cells will rapidly begin producing new bone while other natural process slowly degrade and remove the specialized ceramic matrix. The cell-seeded prosthesis is then implanted at the trauma site and appropriate rehabilitation therapy is begun.

Figure 1:
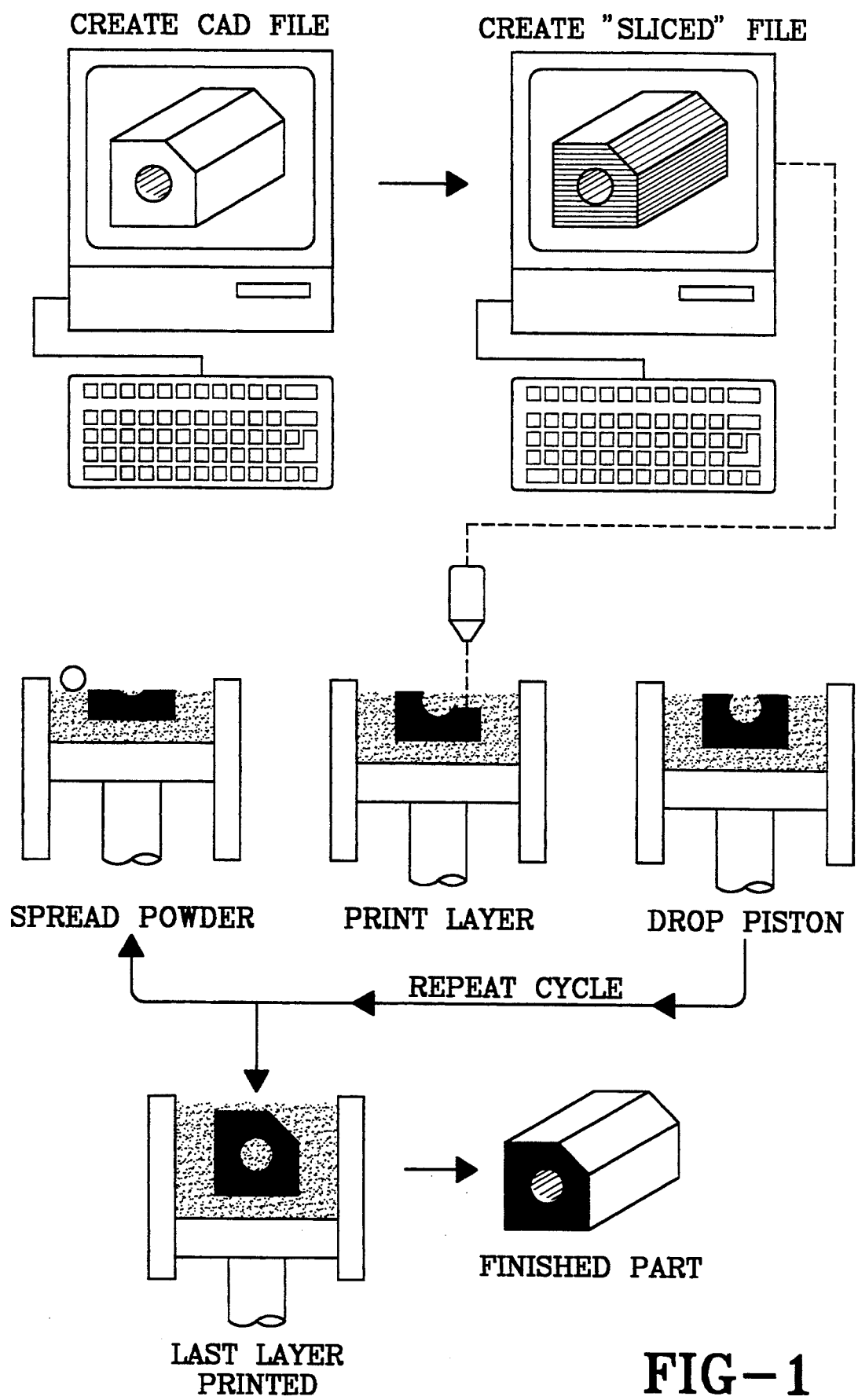
FIG. 1 is a diagram illustrating the MIT powder process.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

The invention is a new manufacturing approach that will provide customized prosthetic devices for hard tissue reconstruction. Free-Form Manufacturing (FFM) technology is a valuable new tool for making implants that reproduce original tissue size and shape, and that maximize the rate of cell-mediated hard tissue healing. The concept requires integration of several independently developing technologies into the FFM system.

This strategy for reconstruction of traumatic, disease-related or surgical loss of hard tissue is based on the hypothesis that therapy will be optimally treated by a prosthesis that:
1. is matched to the precise anatomical dimensions of the original tissue (or that may be modified to compensate for anticipated healing responses or to provide for surgical-assist structures);
2. is composed of a ceramic material that exhibits properties similar to bone, and that presents physical, chemical and surface properties that facilitate bone cell function and production of new bone;
3. is designed to maximize the rate of cellular colonization of the ceramic matrix and to direct the production of new bone—alternatively, a more active approach is to optimize the device for seeding by autologous cells derived from the patient.

Manufacturing steps in the process will include:
1. specification of the physical properties of the customized prosthetic device by use of available computerized imaging techniques (for example, Computerized Tomography, CT, or Magnetic Resonance Imaging, MRI) to produce a solid model "design file" or CAD file. This specification may also involve secondary manipulation of the files to assist in surgical implantation and/or to compensate for, or optimize, anticipated healing processes;
2. development of a mathematically processed design file to produce a "sliced file" suitable for directing an FFM process;
3. construction of a precise replica of the sliced file by FFM in an appropriate ceramic material to produce the implant.

This is an integrated system for imaging hard tissue, manipulating the image file to produce the design file, processing the design file to drive the FFM system and produce the implant, and optimizing the surgical implantation and performance of such devices. It provides a method for fabricating customized medical implant devices. This technology will be used by the general orthopedic and dental communities as a specialized service.

The glass, glass-ceramic or calcium phosphate materials described above in the Background Art may be used. Additionally, implant devices may also be constructed from calcium carbonate, a resorbable ceramic, alumina or other biocompatible ceramics. Unique ceramic processing may be required for each specific approach. In the $Al_2O_3/NH_4H_2PO_4$ system, for example, alumina has a melting point of 2045° C., while $NH_4H_2PO_4$ has a melting point of 190° C. Crystalline materials like ammonium phosphate and boron oxide show a definite melting point which the viscosity drops sharply. When the alumina/ammonium phosphate blend is processed with the DTM laser, the lower-melting-point phosphate melts to form a glassy material and bonds the alumina particles. A secondary heat treatment is necessary to develop the full strength of the material. During heat treatment at 850° C., the following net reaction takes place.

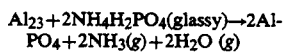

$$Al_2O_3 + 2NH_4H_2PO_4(glassy) \rightarrow 2AlPO_4 + 2NH_3(g) + 2H_2O(g)$$

The reaction results in an $Al_2O_3/AlPO_4$ composite where aluminum phosphate forms a thin layer around the alumina particles. The $AlPO_4$ volume fraction depends on the initial composition.

FFM technology presents a unique capability to introduce a defined porosity into ceramic devices formed by aggregation (sintering) of particulate substrates. For example, the porosity might be introduced or modified: 1. by direct reproduction of a "porous" CT file; 2. by varying the particle size distribution of the base ceramic; or 3. by post-treatment of formed devices to remove specific agents included in the original mixed-particulate bed (e.g., by differential solubility). These processes offer a range of porosities available to tailor FFM devices to specific applications.

Figure 2:
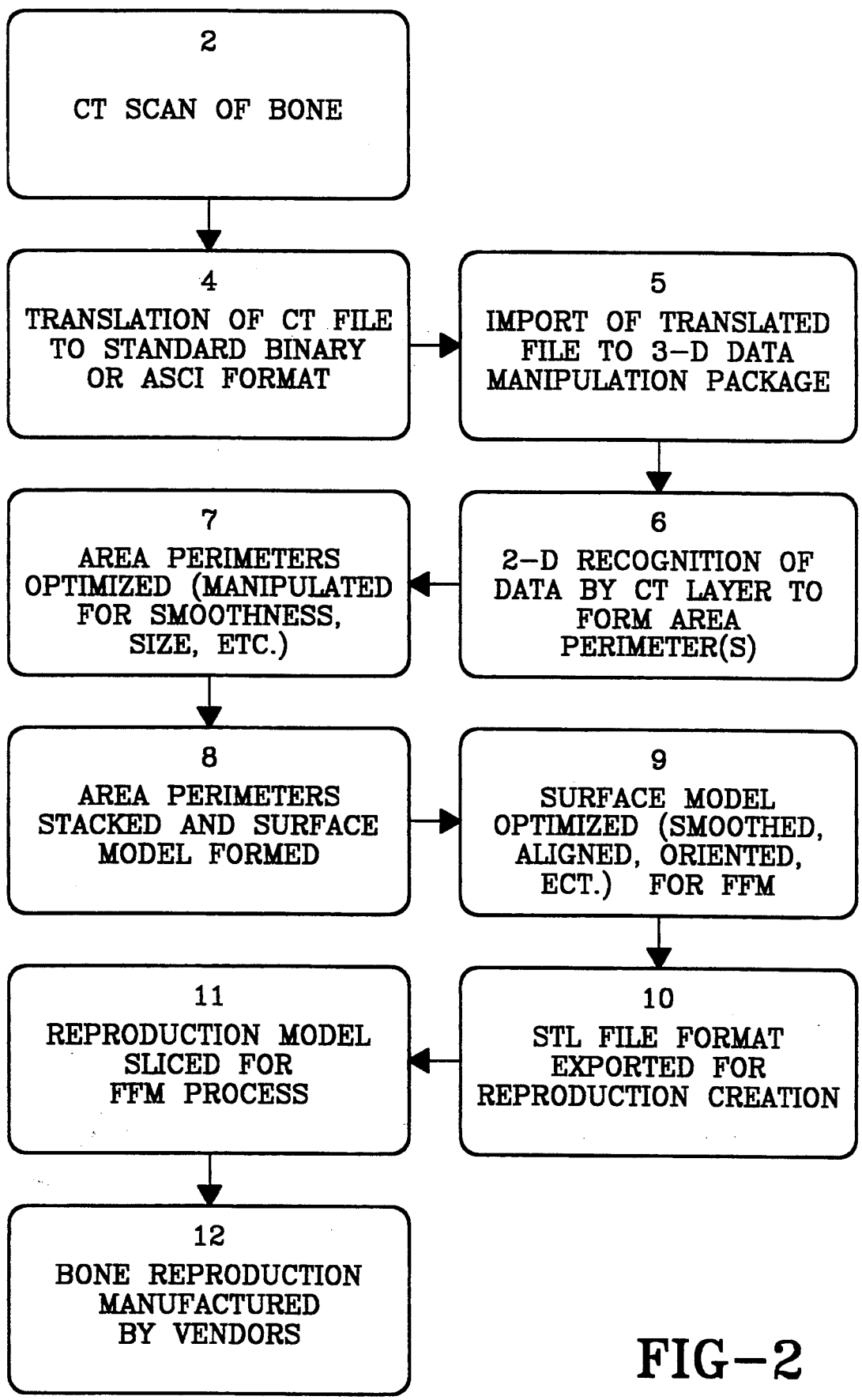
FIG. 2 is a flow chart illustrating the method of the present invention.

The transformation of a CT bone image to a polymeric FFM reproduction may also be done using photoactive polymer techniques. In such a technique a monomer is polymerized at selected regions by an incident laser beam to create a solid polymeric model. The approach for the fabrication of ceramic devices is outlined in FIG. 2. Thus, fluid materials, either liquids or masses of particles, are used to fabricate the replica of the bone.

One key aspect of this manufacturing technique is the segmentation process, in which the "bone" is recognized and separated from the other tissues in the image, and the reproduction of a smooth bone surface, which entails the manipulation of the data after segmentation.

The fluid materials may be ceramic particles which are sintered to form the solidified replica using a DTM process. Ceramic particles may be cemented together with a second type of ceramic particles or with a polymeric phase. The replica may be formed by a laser photo polymerization process (e.g. 3 D systems) in which ceramic particles are suspended in a liquid monomer and then became trapped in the liquid polymer after polymerization. Thereafter, a part or all of the polymer may be removed. In addition, with the above processes in which the precursors of the final ceramic product are formed by FFM methods, the resulting solid replica may be converted to a desired composition. For example, the replica may be formed of calcium carbonate or tricalcium phosphate and then converted to hydroxyapatite by conventional processing techniques.

While certain preferred embodiments of the present invention have been disclosed in detail, it is to be understood that various modifications may be adopted without departing from the spirit of the invention or scope of the following claims.

We claim:

1. A method for fabricating an implantable device, the method comprising:
fabricating an approximate replica of bone by sequentially solidifying adjoining, cross-sectional intervals of a fluid material along an axis.

2. A method in accordance with claim 1 wherein a design data base is first generated by scanning at least a portion of an animal's body using imaging techniques to generate a design data base of measurement data representing size and shape of the bone in a three dimensional coordinate system and then fabricating said replica in correspondence with the data in said design data base.

3. A method in accordance with claim 2 wherein the step of solidifying a fluid material comprises bonding ceramic particles.

4. A method in accordance with claim 2 wherein the scanning step comprises generating the data base by scanning a body part of a healthy individual animal and archiving the data base for subsequent use.

5. A method in accordance with claim 4 wherein the method further comprises modifying the data base to make selected changes in the size and shape of the bone represented by the data base.

6. A method in accordance with claim 1 wherein the step of solidifying a fluid material comprises bonding a photo-active polymeric material.

7. A method in accordance with claim 1 wherein the step of solidifying a fluid material comprises sintering ceramic particles.

8. A method in accordance with claim 1 wherein the step of solidifying a fluid material comprises bonding particles a first ceramic material together with particles of a second ceramic material.

9. A method in accordance with claim 1 wherein the step of solidifying fluid material comprises cementing particles together with a polymer.

10. A method in accordance with claim 1 wherein the fluid material comprises ceramic particles suspended in a liquid monomer and wherein the monomer is polymerized to form a solid polymer network and wherein at least a part of the polymer is then removed.

11. A method in accordance with claim 1 wherein the fluid material comprises ceramic particles and wherein the solidified replica is then reacted with an agent to change its composition.

12. A customized implantable device prepared by the method of claim 1.

13. A customized implantable device prepared by the method of claim 2.

* * * * *

(12) EX PARTE REEXAMINATION CERTIFICATE (5389th)
United States Patent
Fink et al.

(10) Number: US 5,370,692 C1
(45) Certificate Issued: Jun. 6, 2006

(54) RAPID, CUSTOMIZED BONE PROSTHESIS

(75) Inventors: David J. Fink, Marble Cliff, OH (US); Salvatore T. DiNovo, Columbus, OH (US); Thomas J. Ward, Columbus, OH (US)

(73) Assignee: Bioz, LLC, Columbus, OH (US)

Reexamination Request:
No. 90/006,709, Jul. 14, 2003

Reexamination Certificate for:
Patent No.: 5,370,692
Issued: Dec. 6, 1994
Appl. No.: 07/929,449
Filed: Aug. 14, 1992

(51) Int. Cl.
*B29C 35/08* (2006.01)
*A61F 2/28* (2006.01)

(52) U.S. Cl. ........................ 128/898; 264/401; 264/494; 600/587; 700/120; 623/901; 623/914

(58) Field of Classification Search .............. 623/23.56, 623/23.58, 23.63, 23.5, 23.51, 923, 911
See application file for complete search history.

(56) References Cited

U.S. PATENT DOCUMENTS 4,936,862 A 6/1990 Walker et al.
4,940,412 A * 7/1990 Blumenthal ................. 434/267

OTHER PUBLICATIONS

S.J. Bresina et al., *Automated Production of Custom Bone Replacements*, Article, Annual International Conference of the IEEE Engineering in Medicine and Biology Society, vol. 12, No. 1, 1990, 2 pgs.
Stephen J. Rock et al., *Utilizing Topological Information to Increase Scan Vector Generation Efficiency*, Article, RPI Rensselaer Design Research Center, Rensselaer Polytechnic Institute, 1991, pp. 28–36.
Michael J. Cima et al., *Three Dimensional Printing: Form, Materials, and Performance*, Article, Massachusetts Institute of Technology, Department of Materials Science and Mechanical Engineering, undated, pp. 187–194.

* cited by examiner

*Primary Examiner*—David H. Willse

(57) ABSTRACT

Prosthetic bone implants are fabricated to approximately replicate a patient's original bone. Medical computer aided imaging techniques are applied to generate a data base representing the size and shape of the original bone in a three dimensional coordinate system. The implantable replica is fabricated using the data base and free form manufacturing to sequentially solidify adjoining, cross-sectional intervals of a fluid material. Appropriate fluid materials include ceramic particles which may be selectively bonded by sintering or bonding with a polymer, and a monomer which is polymerized at selected regions by an incident laser beam.

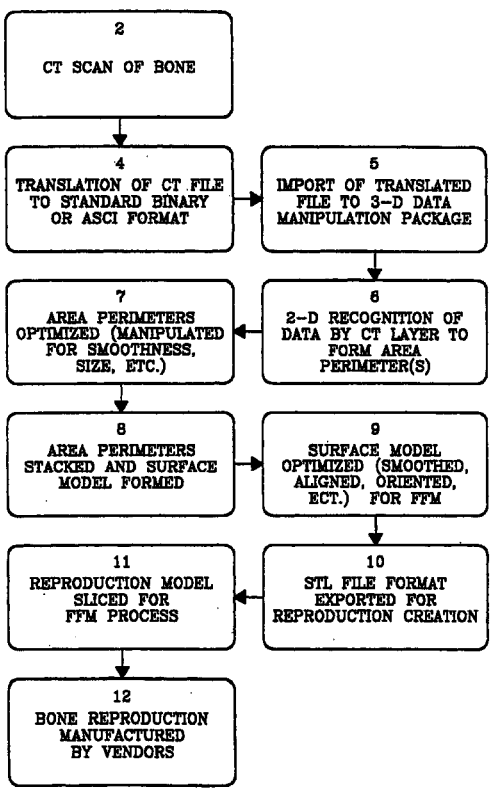

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–13 are cancelled.

* * * * *